(12) United States Patent
Donitzky et al.

(10) Patent No.: US 6,585,375 B2
(45) Date of Patent: Jul. 1, 2003

(54) METHOD FOR PRODUCING AN ARTIFICIAL OCULAR LENSE

(75) Inventors: Christof Donitzky, Eckental (DE); Maximilian Reindl, Heroldsberg (DE)

(73) Assignee: Wavelight Laser Technologies AG, Erlangen (DE)

(*) Notice: Subject to any disclaimer, the term of this patent is extended or adjusted under 35 U.S.C. 154(b) by 0 days.

(21) Appl. No.: 09/937,890

(22) PCT Filed: Feb. 16, 2001

(86) PCT No.: PCT/EP01/01746

§ 371 (c)(1),
(2), (4) Date: Oct. 2, 2001

(87) PCT Pub. No.: WO01/60240

PCT Pub. Date: Aug. 23, 2001

(65) Prior Publication Data

US 2002/0154271 A1 Oct. 24, 2002

(30) Foreign Application Priority Data

Feb. 16, 2000 (DE) .......................................... 100 06 896

(51) Int. Cl.[7] ................................................. A61B 3/00
(52) U.S. Cl. ........................ 351/219; 264/400; 623/6.11
(58) Field of Search ................................. 351/205, 212, 351/246, 219; 264/400; 623/4.1, 5.11, 6.11

(56) References Cited

U.S. PATENT DOCUMENTS

| | | | | |
|---|---|---|---|---|
| 4,575,373 A | * | 3/1986 | Johnson | 623/6.22 |
| 4,932,970 A | * | 6/1990 | Portney | 623/6.25 |
| 5,777,719 A | * | 7/1998 | Williams et al. | 351/212 |
| 5,840,219 A | * | 11/1998 | Nguyen | 264/2.7 |
| 6,015,511 A | * | 1/2000 | Yasuda et al. | 264/1.7 |

* cited by examiner

Primary Examiner—Marvin M. Lateef
Assistant Examiner—John R Sanders
(74) Attorney, Agent, or Firm—Clifford W. Browning; Woodard, Emhardt, Moriarty, McNett & Henry LLP

(57) ABSTRACT

A method of producing intra-ocular lenses or contact lenses including the following steps:

a) mechanically forming a lens blank such that it is suitable for correcting an ametropic visual defect, b) measuring the aberration of an eye to be corrected, c) calculating an ablation profile with respect to the lens blank on the basis of the measured aberration, and d) ablating material of the lens blank in accordance with the calculated ablation profile by means of laser radiation.

4 Claims, 3 Drawing Sheets

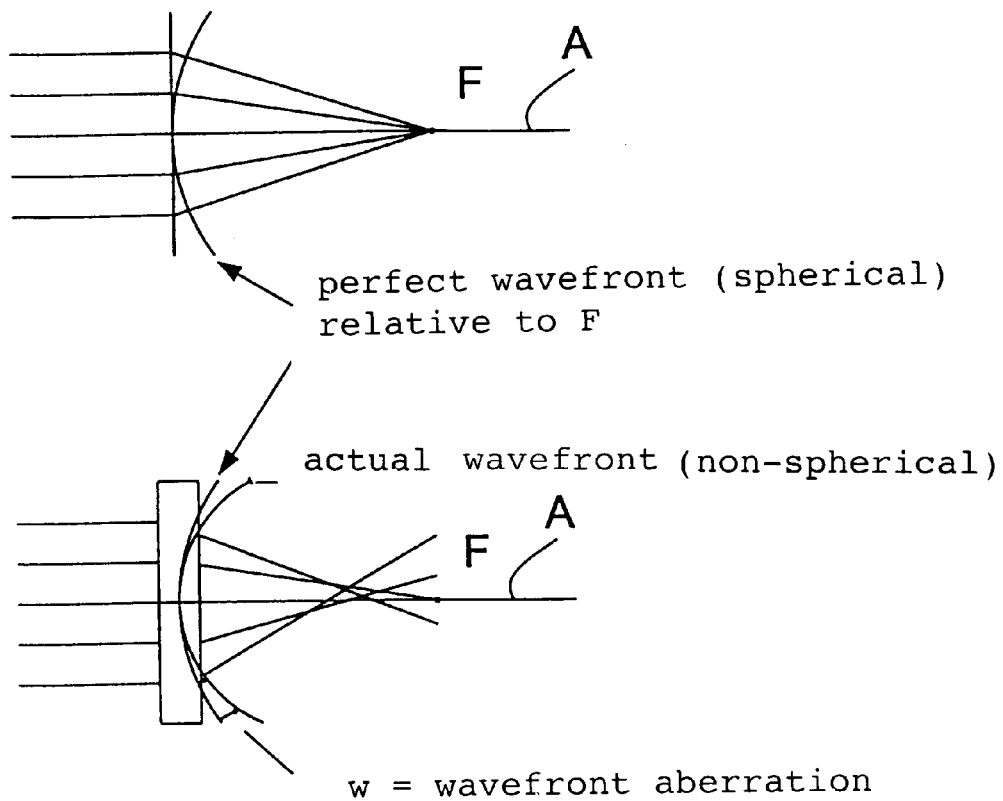
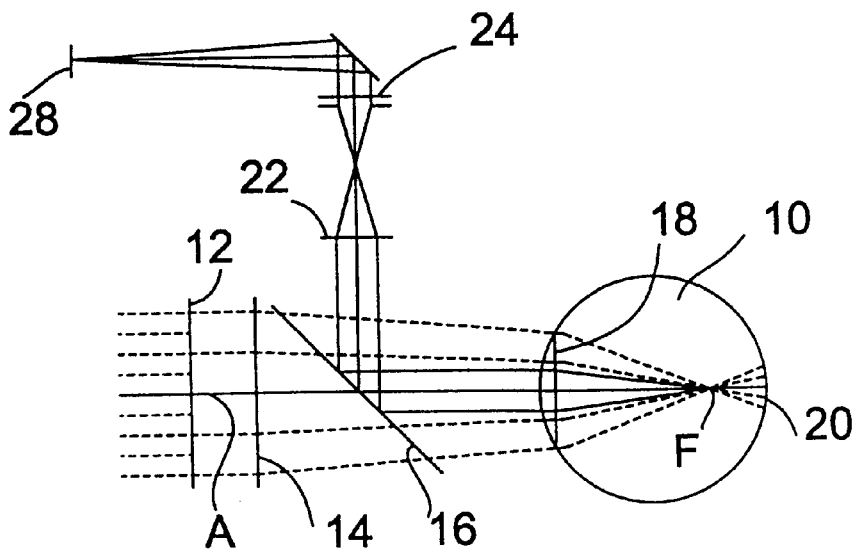

METHOD FOR PRODUCING AN ARTIFICIAL OCULAR LENSE

The present invention relates to a method of producing an intra-ocular lens or a contact lens.

BACKGROUND OF THE INVENTION

Intra-ocular lenses (IOLs) are artificial eye lenses consisting e.g. of acrylic glass, in particular "Plexiglas", or polymethyl methacrylate (PMMA), in particular in the form of a material offered under the name of Acrysoft (trademark). Also silicone is used as a material for IOLs.

Intra-ocular lenses serve to correct refractive errors of the eye, often after a removal of the natural lens. IOIs are also used for correcting high-order visual defects. Also for remedying aphakia IOLs are becoming increasingly important.

The implantation of an IOL is a microsurgical operation carried out either in one session (primary implantation) or in more than one session with insertion of the lens into the apha-kial eye.

Hundreds of different types of intra-ocular lenses are known. These lenses are normally roughly classified according to the positioning of the IOL and its fixation in the eye. A distinction is made between "anterior chamber lenses"; "iris clip lenses"; "posterior chamber lenses fixed in the sulcus (posterior chamber angle)"; and "posterior chamber lenses fixed in the capsular sac". The present invention relates in particular to all these intra-ocular lenses.

Furthermore, the present invention also relates to contact lenses, i.e. optical lenses acting as a visual aid in contact with the eye. A contact lens is optimally adapted to the individual shape of the front section of the eye with its inner surface facing the eye. It serves to correct visual defects and irregular refractive errors, normally refractive errors of the cornea of the eye. Materials which are adapted to be used for contact lenses are in particular PMMA and modifications thereof, CAB (cellulose acetobutyrate), silicone methacrylates, fluorosilicone acrylates, fluorocarbons, HEMA hydrogels, etc.

In the prior art, intra-ocular lenses as well as contact lenses are normally formed at the manufacturer's, then delivered to the hospital or the ophthalmologist where they are inserted in or attached to the patient's eye, i.e. the lenses are mechanically formed and, optionally, polished, packed in a sterile condition and then delivered to the hospital or the ophthalmologist who inserts the respective lens in the patient's eye.

Intra-ocular lenses especially serve to correct myopia, hyperopia, and astigmatism. For this purpose, the so-called refraction data of the patient's eye are measured, i.e. the dioptric value measured for the patient's eye determines the shape of the lens. In accordance with this measurement, the ophthalmologist then orders or takes from a stock a specific intra-ocular lens corresponding to this dioptric value of the patient. It follows that this conventional method is in this sense an "overall correction" of lower-order visual defects insofar as the correction is based on the "overall" dioptric value of the eye.

Optical image formation in the eye is, however, not only impaired by the above-mentioned lower-order visual defects but also by so-called higher-order image errors. Such higher-order image errors occur especially after operations on the cornea and within the eye (cataract operations). Such optical aberrations may be the cause for the fact that, in spite of a medical correction of lower-order defects, the full visus is not achieved. P.Mierdel, H.-E. Krinke, W. Wigand, M. Kaemmerer and T. Seiler describe in "DER OPHTHALMOLOGE", No. 6, 1997, p. 441, a measuring set-up for determining the aberration of the human eye. By means of such a measuring set-up, aberrations (imaging errors) for monochromatic light can be measured. The aberrations that can be measured are not only aberrations caused by the cornea, but what can be measured are the imaging errors caused by the whole ocular image-forming system of the eye, said measurements being carried out in a position-dependent manner, i.e. for given locations within the pupil of the eye it can be determined with a specific resolution how large the imaging error of the whole optical system of the eye to be corrected is at this location. Such imaging errors of the eye are mathematically described in the above-cited paper of P. Mierdel et al. as so-called wave-front aberration. A wave-front aberration is the three-dimensional profile of the distance between a real light wave front of a central spot of light and a reference surface, e.g. an ideal spherical shape, i.e. the system used as a spatial reference system is e.g. the spherical surface of the ideal wave front. It is, in principle, also known in the prior art to choose a plane as a reference system for the aberration measurement, in cases in which the ideal wave front to be measured is flat.

BRIEF SUMMARY OF THE INVENTION

When realizing the present invention, the measurement principle according to the above-mentioned paper of P. Mierdel, T. Seiler et al. can also be used as an initial step. The essential features here are that a parallel bundle of light of sufficient diameter is subdivided into separate parallel single rays by a perforated mask. These single rays pass through a collective lens (a so-called aberroscope lens) and are thus focussed in front of the retina at a specific distance therefrom in the case of an emmetropic eye. This leads to easily visible projections of the mask holes on the retina. This retinal light spot pattern is imaged on the sensor area of a CCD video camera according to the principle of indirect ophthalmoscopy. In the aberrationfree ideal eye the imaged light spot pattern is orthoscopic and corresponds precisely to the perforated mask pattern. If, however, an aberration exists, this will result in individual displacements of each pattern spot, since each single ray passes through a specific area of the cornea and pupil, respectively, and undergoes a deviation from the ideal path in accordance with the irregular optical effect. From the retinal pattern spot displacements, the wave-front aberration is finally determined with an approximation method as a local function over the pupil area. The above-cited prior art also describes the mathematical representation of this wave-front aberration in the form of a so-called "wave-front aberration mountain". This wave-front aberration mountain indicates over each pupil location (x-y coordinates) a value for the wave-front aberration $W(x, y)$ which is then plotted as height against the x-y coordinates. The higher the "mountain", the higher the imaging distortions in the eye at the respective pupil location. For each incident light beam there is a proportionality between the measured deviation of the respective retinal light spot from its ideal position and the steepness of the "wave-front aberration mountain" in a first approximation. It follows that the wave-front aberration can be determined therefrom as a local function related to an arbitrary reference value on the optical axis of the system. Ideal, normally undistorted light spot positions on the retina, which can provide the reference value, are e.g. four central, closely spaced spots. Such spots represent a central cornea-pupil zone having a diameter of approx. 1 to 2 mm; from previous experience, it can be assumed that this zone is largely free from higher-order image errors.

The "wave-front aberration mountain" can be mathematically represented in different ways with the aid of a complete term (a function). Terms which can be used for this purpose are e.g. approximations in the form of a sum of Taylor polynomials or especially also Zernike polynomials. The Zernike polynomials have the advantage that their coefficients are directly related to the generally known image errors (spherical aberration, coma, astigmatism, distortion). The Zernike polynomials are a set of fully orthogonal functions. In a paper of J. Liang, B. Grimm, S. Goelz and J. F. Bille, "Objective measurement of wave aberrations of the human eye with the use of a Hartmann-Shack wave-front sensor, *Optical Society of America*, 11(7): 1949–1957, July 1994, it is shown how the wave front (or rather the wave-front aberration) can be calculated from the grid-point displacements. The actual wave front can be determined in this way from the determination of the derivative function of the wave front. The wave front is obtained as solution of a system of equations. Also the paper of H. C. Howland and B. Howland "A Subjective Method for the Measurement of Monochromatic Aberrations of the Eye", *Journal of the Optical Society of America*, 67(11): 1508–1518, November 1977, describes a method of determining the monochromatic aberration and the determination of the first fifteen Taylor coefficients. This prior art can be resorted to.

In WO 99/27334 the wave-front aberration of the eye is measured and used for the subsequent ablation.

The prior art also describes the attempt to determine ablation profiles individually, in a position-dependent manner, for an eye to be corrected, said determination being based on so-called topographic measurements of the cornea surface, cf. C. E. Martinez, R. A. Applegate et al. in ARCH OPHTHALMOL/Vol. 116, August 1998, pp. 1053–1062. However, such topographies of the cornea surface only provide data on the corneal curvature, i.e. height data at each point of the cornea surface. While it is true that these data can be used for calculating aberrations, they only supply information on higher-order aberrations on the cornea surface, without providing aberration values for the whole optical system "eye". The visual discrimination of the eye (visus) is, however, not only determined by the cornea surface but by the whole optical system of the eye to be corrected (e.g. also the crystalline lens) so that an improvement is desirable also insofar.

It is the object of the present invention to provide a method for economically producing intra-ocular lenses and contact lenses in the case of which the lenses also take into account individual higher-order aberrations of the eye.

Methods according to the present invention by means of which this object can be achieved are characterized in the independent claims.

According to the present invention, a so-called lens blank is first produced mechanically in a conventional manner. The term "mechanical" should here comprise all manufacturing methods which are not based on the ablation (removal) of material by means of laser radiation. The lens blanks can e.g. be cast, pressed or mechanically formed in some other way and, optionally, they can be polished subsequently. This forming of the lens blank takes place such that the lens blank is designed in accordance with an overall dioptric value of the eye to be corrected, e.g. according to the measured dioptric value of the eye, without taking into account higher-order aberrations of the eye, like those that can be determined by the above-described measurement of the wave-front aberration. Such lens blanks can then be delivered by the manufacturer to the site where they are to be used, e.g. hospitals and ophthalmologists, in a sterile type of packing.

On site, i.e. at the hospital or ophthalmological practice, the wave-front aberration of the whole optical system of the eye to be corrected can then be measured with an aberro-scope according to a further step of the present invention. This measurement determines individual refractive properties of the eye, in dependence upon the location within the pupil, thus permitting further processing of the lens blank obtained in the manner described hereinbefore, so as to take into account higher-order aberrations of the eye, by subjecting the lens blank on site to further processing in accordance with the measured aberration data. A system which is particularly suitable for such further processing of the lens blank is a laser system which is available at the hospital or ophthalmological practice anyhow and which is normally used for other purposes, e.g. for shaping the cornea, (e.g. PRK, in particular LASIK). Such laser systems emit wavelengths which can be used for re-shaping not only the cornea of the eye by a removal of material (ablation) but, to a large extent, they can also be used for re-shaping lens material for the above-explained intra-ocular lenses or contact lenses. The invention can also be used by opticians who possess a suitable laser system, i.e. the optician obtains the lens blank and subjects it to further processing according to the present invention.

The data of the individual eye to be corrected, which have been obtained by the measurement of the wave-front aberration, are inputted in a computer; so are the data of the lens blank which, as has already been stated, has been prepared for the correction of an ametropic visual defect, e.g. myopia, hyperopia or astigmatism.

The computer is then programmed in such a way that it calculates on the basis of the two data of the above-mentioned type (i.e. data of the lens blank on the one hand and data of the measurement of the wave-front aberration on the other) an ablation profile with respect to the given lens blank, i.e. it calculates a further shaping of the lens blank in such a way that, after having been inserted in or attached to the eye, the lens body, which has been subjected to suitable further shaping by means of laser radiation, will largely correct the lower-order aberrations (myopia, hyperopia or astigmatism) as well as the individual higher-order aberrations of the eye, i.e. local refractive properties of the "overall system" eye with irregular optical effects.

The ablation of material of the lens blank by means of laser radiation takes place remote from the patient's eye, i.e. not in a condition in which the lens is inserted in or attached to the eye.

It is also possible to calculate in the step of calculating the ablation profile not only the ablation profile with regard to the lens blank but also a further ablation profile, viz. an ablation profile concerning the cornea of the eye into which the lens is to be inserted or to which the lens is to be attached. According to this variant of the invention, an intra-ocular lens or a contact lens is obtained, which carries out part of the correction, whereas the rest of the correction is effected by re-shaping the cornea (again by means of laser radiation). For the latter shaping of the cornea, conventional techniques are available, especially LASIK. The lens shaped in this way can be inserted into the eye before or after the ablation of cornea material.

The fact that the present invention is so conceived that the production is divided firstly into a standardized lens blank and, secondly, into an "after-treatment" of this lens blank with laser radiation on site at the hospital, the ophthalmological practice or at the optician's has the advantage that the production of the lens, which is finally inserted into the eye, is substantially simplified (and therefore much less expensive). Stockkeeping for the hospital or the practice is substantially simplified as well.

BRIEF DESCRIPTION OF THE DRAWINGS

In the following, an example of the present invention will be explained in detail making reference to the drawing, in which:

FIG. 1 shows a schematic representation of the wave-front aberration;

FIG. 2 shows a schematic representation of an aberroscope for measuring the wave-front aberration of the whole optical system of an eye to be treated.

DETAILED DESCRIPTION OF THE INVENTION

Figure 3:
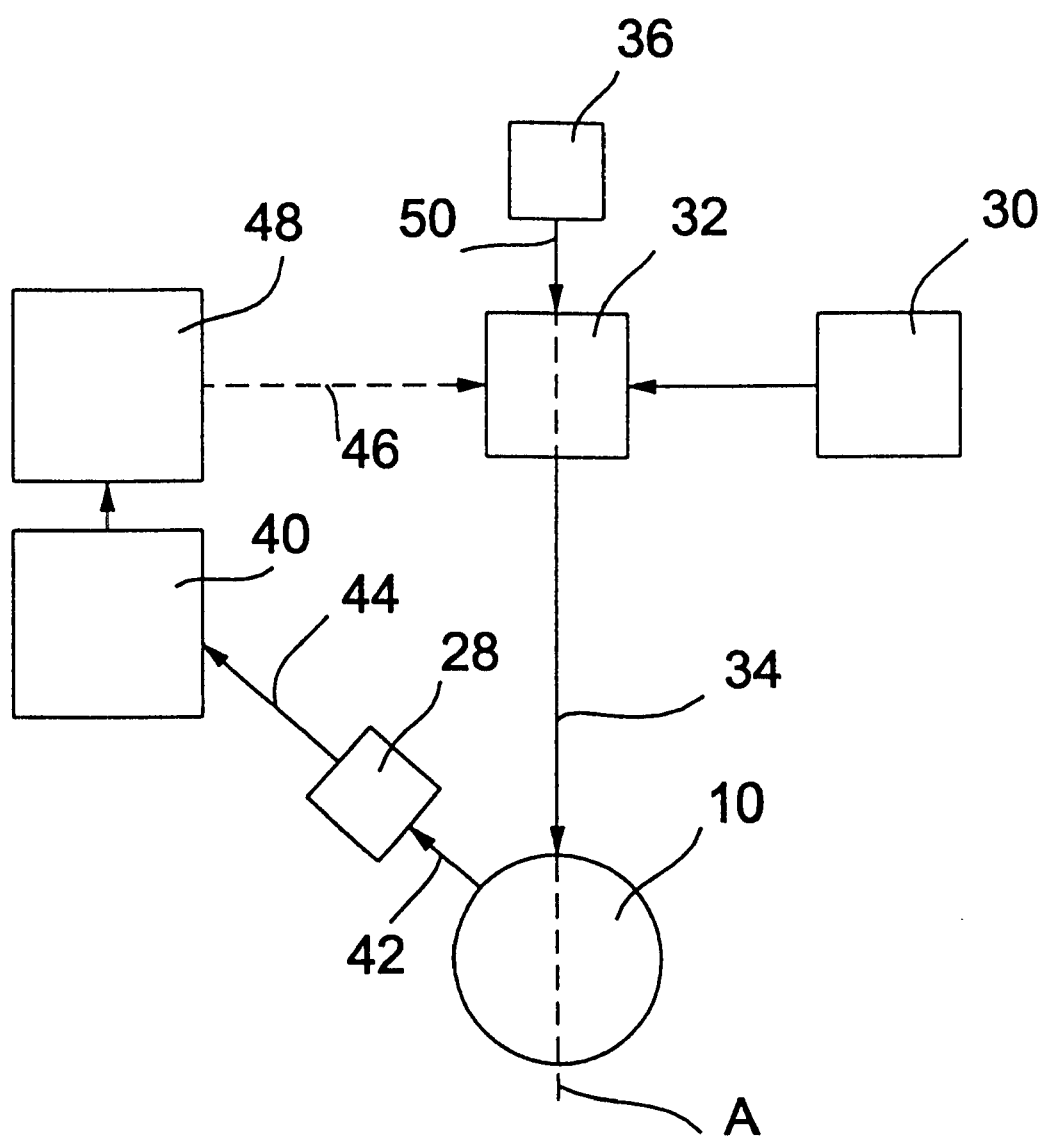
FIG. 3 shows a schematic representation of a measurement and control arrangement for carrying out a photorefractive keratectomy of the eye, means for deriving a photo-ablation profile and means for controlling the laser radiation.

FIG. 1 shows schematically the wave-front aberration of an eye which has already been explained hereinbefore, i.e. the deviation of the real aspherical wave front from the ideal wave front. A is the optical axis of the system and F is the focus; the latter is here also the imaginary starting point of the radiation in the case of an ideal wave front.

FIG. 2 shows schematically the optical scheme of a video aberroscope for measuring the wave-front aberration of an eye 10. The green light of an He—Ne laser (543 nm) is expanded to a diameter of approx. 12 mm and a perforated mask 12 having formed therein a plurality of equidistant holes is then used for dividing this light beam into a corresponding number of parallel single rays. According to FIG. 2, these single rays, which are indicated only schematically by dashed lines, extend parallel to the optical axis A of the system. By means of an aberroscope lens 14 (collective lens) in front of the eye 10, these rays are refracted in such a way that they are focussed in front of the retina 20 at a specific distance therefrom (focus F). In the case of an eye having normal vision, the aberroscope lens has a dioptric power of e.g. +4 dpt. In an aberrationfree ideal eye, a completely undistorted light-spot pattern is formed on the retina 20 in this way. The pupil is designated by reference numeral 18.

If the eye 10, however, shows an aberration, the pattern spots will be displaced in accordance with the imaging errors, since each single ray passes only through a very specific location of the pupil 18 and undergoes a deviation from the ideal path in accordance with the irregular optical effects. This deviation from the ideal path corresponds to the optical imaging error of the whole optical system of the eye 10 with regard to one light ray which passes said specific location within the pupil. On the cornea the single rays are spaced-apart at a constant distance of 1.0 mm e.g. in the x- and y-directions and the ray diameter is e.g. 0.5 mm. The dimension of the whole parallel measuring beam on the cornea is e.g. 8×8 mm.

By means of a semireflecting mirror 16 the light spot pattern produced on the retina 20 is imaged via an ophthalmoscopic lens 22 and a lens 24 for the retinal image on a sensor surface 28 of a solid-state video camera (CCD camera) so as to compute numerically the resultant light spot pattern. The deviations of the light spot locations, related to the equidistant, regular structure of the aberrationfree eye, provide the possibility of determining the wave-front aberration W (x, y) as a local function over the pupil area of the eye. The local function can be approximated by means of a set of polynomials, e.g. Taylor polynomials or Zernike polynomials. The Zernike polynomials are here preferred because their coefficients $C_i$ have the advantage of being directly related to the image errors, such as spherical aberration, coma, astigmatism, distortion. By means of the Zernike polynomials $Z_i$ (x, y) the wave-front aberration W can be represented as follows:

$$W(x, y) = \Sigma_i C_i \times Z_i(x, y).$$

(x, y) stands for the Cartesian coordinates in the pupil plane.

A determination of e.g. the first 14 coefficients $C_i$ (i=1, 2, ..., 14) of the Zernike polynomials permits a sufficiently precise description of the wave-front aberration W(x, y) as a function of the local coordinates of the free pupil area. In this way, a so-called wave-front aberration mountain is obtained, i.e. in a three-dimensional representation a function over the local coordinates x, y which indicates the respective local imaging error. In addition to the Zernike polynomials also other possibilities can be chosen for mathematically describing the wave front, e.g. Taylor series. The Zernike polynomials are only the embodiment which has been chosen here.

From this wave-front aberration W(x, y) a so-called photo-ablation profile is calculated by means of a computer 48 (FIG. 3).

Figure 4:
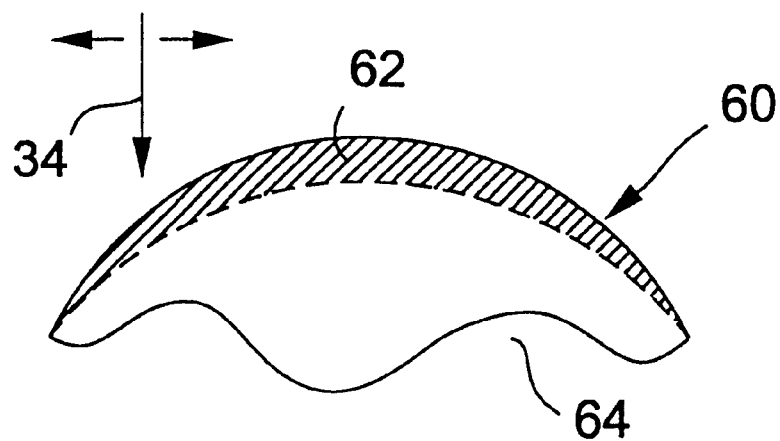
FIG. 4 shows a schematic representation of a lens blank.

According to a first variant of the present invention, this photo-ablation profile refers to a lens blank 60 of the type shown schematically and by way of example in FIG. 4. FIG. 4 shows a lens blank 60 for an intra-ocular lens, only the optical components of the lens being shown in said figure because these are the only components which are of interest in the present connection. Possible fastening means and special embodiments of the lens for fixing it on or for inserting it in the eye have been omitted in the representations according to FIGS. 4 and 5.

The lens blank 60 consists of a material which is adapted to be ablated (removed) by means of laser radiation, especially laser radiation in the UV region (e.g. 193 nm). The materials mentioned at the beginning for IOL and contact lenses are suitable to be used for this purpose to a large extent.

According to the fist variant of the present invention, the computer calculates from the above-explained light spot pattern the wave-front aberration in the form of a certain number of Zernike coefficients and then from said wave-front aberration a photo-ablation profile, i.e. data indicating down to which depth lens material must be ablated at the respective location of the lens so as to reduce the wave-front aberration. The ablation profile is hatched in FIG. 4 and designated by reference numeral 62. It follows that the ablation profile describes the layer thickness of the material to be removed in dependence upon the location (x-y coordinates) and it can be determined from the wave front (aberration) in different ways: the ablation profile for an eye to be corrected is fundamentally calculated on the basis of a suitable model of the eye.

For this purpose, the wave-front aberration is mathematically projected onto the corneal surface with due regard to the geometrical properties of the eye, such as the thickness of the cornea, the distance between the posterior surface of the cornea and the anterior surface of the lens, the distance between the anterior surface of the lens and the posterior surface of the lens, the distance between the posterior surface of the lens and the retina. Furthermore, the refractive indices of the individual optical elements of the eye are taken into account when the ablation profile is being calculated (e.g. tear film n=1.337, cornea n=1.37, aqueous humour n=1.337, etc.). The wave front essentially describes the transit-time differences of the light, i.e. the optical path. When the optical path is divided by the refractive index, the geometrical path is obtained. It follows that the associated ablation profile can be derived from the projection of the wave front onto the cornea. After the fashion of an iteration, an ablation depth (e.g. in the example according to FIG. 4 the ablation profile 62) is mathematically assumed at the given point of the cornea, and it is calculated which effect such an ablation would have on the transit-time differences of the rays. The aim is an equalization of the transit times of the rays at all locations of the cornea in such a way that the wave-front aberration becomes as small as possible. In this connection, it must be taken into account that the wave front can also assume values whose physical meaning denotes an application of material, which is normally not possible. The ablation profile must therefore be adapted in a suitable manner, i.e. the ablation profile as a whole must be shifted such that the desired target profile of the lens 64 is achieved only by ablation (removal).

Figure 5:
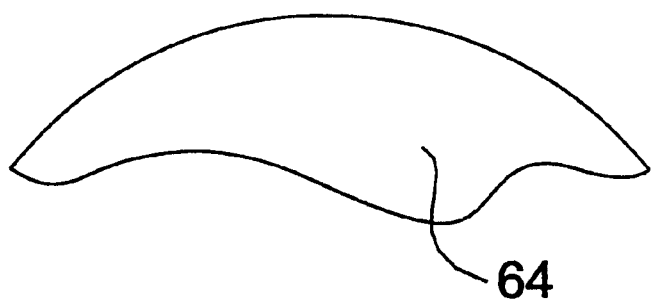
FIG. 5 shows a schematic representation of a finished lens after an ablation of material.

Hence, the ablation profile 62 is ablated by means of laser radiation from the lens blank 60 shown in FIG. 4 so that the intra-ocular lens 64 or contact lens shown schematically in FIG. 5 is obtained, which, in a manner known per se, is either inserted in the eye as IOL or attached to the eye as a contact lens.

According to a modification of the above-described variant of the present invention, another course of action which can be taken when the ablation profile 62 is being calculated is that, in addition to the intra-ocular lens or the contact lens, also the cornea of the eye is re-shaped in a manner known per se (e.g. making use of LASIK). The ablation profile 62 is then modified accordingly with respect to the lens blank 60, i.e. a smaller amount of material will normally be removed from the lens blank, since part of the refraction correction is achieved by re-shaping the cornea.

Alternatively to the above-described possibility of calculating the ablation profile for the lens blank and perhaps the cornea from the wave-front aberration, the ablation profile can also be calculated directly from a projection of spots onto the cornea and the retina. When a light beam falls on the cornea and then into the eye with known incident angles and coordinate points, this light beam will be imaged on the retina in accordance with the optical properties of the eye. Since the position of the light beam on the cornea and the incident angles of the beam are known, the optical path can be reproduced by measuring the position of the light beam on the retina. If this measurement shows that the position of the light beam on the retina deviates from the target position (target position means that the image is aberration-free), the aberration can be determined from the position deviation. The light is refracted in accordance with the geometrical curvature of the surface of the cornea and the other aberrational defects of the system "eye". The above-mentioned position deviation of the light beam on the retina can be expressed by a corresponding change of the incident angle of the light. The incident angle of the light is proportional to the derivative function of the surface of the cornea. By iteration, an (abnormal) change in the curvature of the cornea surface can be concluded from the shifted position of the light beam on the retina and the resultant change in the incident angle of the light. It follows that the change in the curvature of the cornea surface describes the derivative function of the (sought) ablation profile. When this method is executed with a sufficiently large number of light rays at different points of the eye (e.g. by projecting a grid onto the cornea), the whole derivative function of the (sought) ablation profile can be determined. From this the ablation profile can then be calculated with known mathematical methods (e.g. spline interpolation and subsequent integration).

FIG. 3 shows schematically the computer and control system for executing a photo-ablation according to the calculated photo-ablation profile. The photo-ablation is carried out on the surface of the lens blank 60.

A laser which is adapted to be used as a laser 30 for the photo-ablation is especially an Excimer layer (193 nm). Other lasers which can be used for this purpose are especially Er:YAG solid-state layers with a wavelength of 2.94 μm and UV solid-state lasers (e.g. Nd:YAG with 213 nm).

The laser radiation is deflected by means of a galvanometric scanner 32 and the deflected laser beam 34 is directed onto the lens blank 60 so as to ablate the ablation profile 62.

In the above-discussed embodiment, the wave-front aberration was determined by means of grid-point displacement (e.g. according to the paper of J. Liang et al.). It is, in principle, also possible to measure the wave-front aberration in some other way (e.g. according to the above-cited paper of H. C. Howland and B. Howland) or also according to a paper of G. Smith, R. A. Applegate and H. C. Howland *Ophthal. Physiol. Opt.* Vol. 16, No. 3, pp. 222–229, 1996 or the paper of G. Walsh, W. N. Charman and H. C. Howland in *Optical Society of America* 1984, pp. 987–992.

What is claimed is:

1. A method of producing an intra-ocular lens comprising at least the following steps:
    a) mechanically forming a lens blank (60) such that it is suitable for correcting a visual defect selected from the group consisting of myopia, hyperopia, and astigmatism;
    b) measuring the aberration of an eye to be corrected;
    c) calculating an ablation profile (62) with respect to the lens blank (60) obtained by step a) on the basis of the measured aberration; and
    d) ablating material of the lens blank (60) in accordance with the calculated ablation profile (62) by means of laser radiation (34).

2. A method according to claim 1, characterized in that, in addition to the ablation profile (62) with respect to the lens blank (60) of step c, calculating a further ablation profile with respect to the cornea of the eye to which the lens is to be attached or into which the lens is to be inserted.

3. A method of producing a contact lens comprising at least the following steps:
    a) mechanically forming a lens blank (60) such that it is suitable for correcting a visual defect selected from the group consisting of myopia, hyperopia, and astigmatism;
    b) measuring the aberration of an eye to be corrected;
    c) calculating an ablation profile (62) with respect to the lens blank (60) obtained by step a) on the basis of the measured aberration; and
    d) ablating material of the lens blank (60) in accordance with the calculated ablation profile (62) by means of laser radiation (34).

4. A method according to claim 3, characterized in that, in addition to the ablation profile (62) with respect to the lens blank (60) of step c, calculating a further ablation profile with respect to the cornea of the eye to which the lens is to be attached or into which the lens is to be inserted.

* * * * *